United States Patent [19]

Grey et al.

[11] Patent Number: 5,110,746
[45] Date of Patent: May 5, 1992

[54] METHOD FOR THE DETERMINATION OF ALBUMIN IN BIOLOGICAL FLUIDS

[75] Inventors: Howard Grey, Geneva; Ciaran Mangan, Onex, both of Switzerland; Jean Brochot, St. Julien En Genevois, France; Iqbal Siddiqi, Villette, Switzerland

[73] Assignee: Pharmacia Diagnostics Inc., Fairfield, N.J.

[21] Appl. No.: 299,939

[22] PCT Filed: Apr. 22, 1988

[86] PCT No.: PCT/US88/01328

§ 371 Date: Dec. 22, 1988

§ 102(e) Date: Dec. 22, 1988

[87] PCT Pub. No.: WO88/08533

PCT Pub. Date: Nov. 3, 1988

[30] Foreign Application Priority Data

Apr. 22, 1987 [EP] European Pat. Off. ......... 87810253.2

[51] Int. Cl.$^5$ .............................................. G01N 33/50
[52] U.S. Cl. ....................................... 436/88; 436/34; 436/63; 436/71
[58] Field of Search ................... 436/88, 87, 34, 63, 71

[56] References Cited

U.S. PATENT DOCUMENTS 4,013,416 3/1977 Rittersdorf et al. .

FOREIGN PATENT DOCUMENTS

| | | |
|---|---|---|
| 0141298 | 5/1985 | European Pat. Off. . |
| 2304084 | 3/1975 | France . |
| 853643 | 11/1960 | United Kingdom . |
| 1267186 | 3/1972 | United Kingdom . |
| 2118301 | 10/1983 | United Kingdom . |
| 2118304 | 10/1983 | United Kingdom . |
| 8200056 | 1/1982 | World Int. Prop. O. . |

OTHER PUBLICATIONS

N. W. Tietz, "Fundamentals of Clinical Chemistry", 1982, pp. 335–338, Philadelphia, U.S.; W.B. Saunders Co.
Chemical Abstracts, vol. 93, No. 1, Jul. 7, 1980, p. 248, col. 1, Abstract No. 2522r, Joshi et al.
Chemical Abstracts, vol. 87, No. 19, Nov. 7, 1977, p. 192, col. 1, Abstract No. 147477r, R. R. King et al.

*Primary Examiner*—Robert J. Warden
*Assistant Examiner*—Lyle Alfandary-Alexander
*Attorney, Agent, or Firm*—Davis Hoxie Faithfull & Hapgood

[57] ABSTRACT

Serum is reacted with a dinitrohalobenzene compound and the rate of halogen formation is measured. This rate is in proportion to the amount of albumin in the sample. Other proteins like the globulins, as well as free aminoacids and urea, do not interfere with this reaction.

15 Claims, 1 Drawing Sheet

METHOD FOR THE DETERMINATION OF ALBUMIN IN BIOLOGICAL FLUIDS

The present invention relates to a method for quantitatively determining albumin in blood serum even in the presence of globulin and other serum proteins.

Techniques for measuring albumin in blood and other biological fluids, e.g. urine, are important in medicinal, diagnostic and clinical chemistry. Usually, total protein in serum is ascertained by the so-called "biuret/copper reaction" which relates to the formation of colored complexes (violet) between copper $^{+2}$ ions and the peptide bonds of proteins. To separately determine albumin and glubulins the globulins are precipitated by salting out (e.g. with alkali or ammonium sulfate) and separated by centrifugation and thereafter, albumin in the supernatant solution is determined independently, also by the biuret reaction. This technique being time consuming, methods have been developed for the direct determination of albumin in blood serum in the presence of other proteins. For instance, a bromocresol green (BCG) dye-binding procedure for the quantitative determination of serum-albumin was introduced in 1964 by DELANEY (Proc. Australian Assoc. Clin. Biochem 64 (1964), 1). Serum is diluted with buffered BCG at pH 7.0 and the decrease in absorbance at 615 nm is measured. This change in absorbance is linear with albumin concentration up to 50 mg/ml and other electrophoretically separated proteins like hemoglobin and bilirubin do not interfere.

It was however desirable to uncover even more specific techniques, i.e. even less susceptible to disturbance by other molecules in the serum. The method summarized in claim 1 is an important step toward this objective. It was completely unexpected to find that albumin can be quantitatively ascertained by this route, even in the presence of large quantities of globulins. Indeed, reagents of the kind applicable in the present method i.e. o,p-dinitrohalobenzenes are known to undego bimolecular nucleophilic displacement with the NH$_2$-terminal groups of proteins (see Sanger Biochem. J. 39 (1945), 507, 1945), the rate order being F>Cl~Br. Thus, it was surprising, at least in the case when the halogen is fluorine, to note that albumin was practically the only type of protein in blood serum to give appreciable reaction rates even in the presence of the other proteins, e.g. globulins.

Another unexpected finding is that, instead of having to measure the reaction rates by recording changes in some optical or other properties related to complex formation, the reaction was advantageously followed by measuring the amount of fluorine released. This was surprising because although the foregoing reaction (see scheme below) involves fluorine substitution as follows (X represents fluorine):

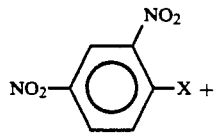

-continued

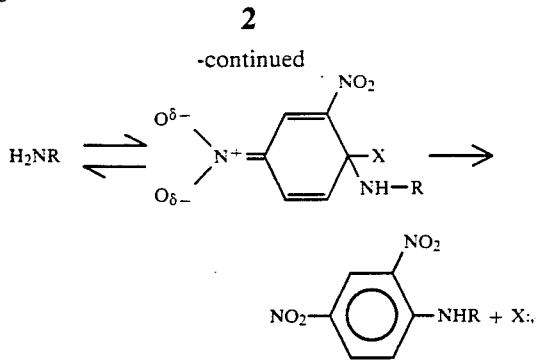

it is not obvious that this should appear in a directly measurable form, e.g. which can be measured with an ion-selective fluoride electrode.

One of the preferred reagents, the dinitro-fluoro-benzene compound (DNFB) is sparingly soluble in water. Therefore, for best results, DNFB organic solutions were emulsified with suitable aqueous buffered media compatible with the serum samples and the reaction was run under such conditions. For example, a solution of DNFB in benzene was emulsified with buffer, (characteristically a 0.1N to 1N solution at pH 5.5-7.7) and the sample of serum to be analyzed was stirred with the emulsion. The evolution of fluoride was followed using a fluoride ion-selective electrode of any conventional type. Calibration curves were obtained by means of a set of standard solutions of albumins and the concentration of unknowns was determined by comparison with the calibration curves. The presence of globulins and other blood proteins as well as free amino acids and urea did not interfere in the range of concentrations normally present in blood serum.

As the organic solvents for the DNFB, ether, toluene, DMF, DMSO, THF, EtOH and MeOH are also suitable but to a lesser extent because some of them behave as nucleophiles and they cause electrode drift.

The choice of the buffer is also important; it was found for instance that with conventional acetate, tris, and cacodylate buffers, in the above-mentioned pH interval, electrode drift occurred while there was no appreciable drift with phosphate buffer (pH 5.8-7.6). Although, the reasons for this difference have not been investigated, it may be tentativelly assumed that organic buffers act as nucleophiles and cause some halogen displacement. Although the present method is operable with organic buffers giving electrode drift (i.e. results are reproducible if the timing of the successive steps is controlled), inorganic buffers, e.g. phosphate are the preferred buffers.

Instead of emulsifying the DNFB reagent with an aqueous buffer to provide the reaction medium, the following alternative procedure was successfully used.

A piece of filter paper was impregnated with the DNFB solution and allowed to dry.

To carry out the analysis, the dried impregnated paper was put on the bottom of a beaker and working buffer solution was added together with a small amount of fluoride and the mixture was magnetically stirred, the electrode was immersed in the solution and, after a period of stabilization, the sample of serum was added and the rate measurement was carried out.

Usually, the reaction rates obtained with known standard albumin solutions are stored in the memory of a microprocessor (connected to a conventional measuring unit for the electrode) and, when operating with a sample of unknown albumin content, the rates are recorded and computed against the stored data, which computation automatically provides the results in terms of concentration of albumin in the sample; the results may be displayed on chart paper or visually on a screen.

The following Examples illustrate the invention in detail.

EXAMPLE 1

A portion of 0.1 ml of 5M DNFB solution in benzene was pipetted onto a Whatman filter paper (2 cm diameter) and the disk was dried in a warm air flow. Several disks were prepared and stored before use.

Calibration samples of albumin were prepared (serum standard), ranging from 10 to 100 mg/ml, in 0.1M phosphate buffer, pH 7.6.

A polypropylene beaker (10 ml) was used to carry out the measurement, together with an F$^-$ selective electrode (Orion combination electrode connected to an Orion 901 ion analyzer interfaced to an Apple II E microcomputer).

The dried filter paper was placed in the bottom of the beaker and 5 ml of the phosphate buffer was added together with 5 $\mu$l of 10$^{-3}$M aqueous NaF (to provide a stable base line potential for the measurement and a rapid return to baseline thereafter). The solution was magnetically stirred and the electrode was immersed therein and allowed to stabilize for about 1-2 min. An aliquot (0.1 ml) of the standard solution was then added and the generation of F$^-$ was measured by recording the change of potential (mV) of the ion selective electrode. The results are reported on the graph in FIG. 2 which indicates in abcissa the concentrations of albumin in mg/ml and, in ordinate, the change of F$^-$ concentration with time ($\mu$mol/l/min) as obtained from the rate curves by means of the NERNST equation.

The same experiments were run in the presence of variable amounts of globulins which showed no interfering effect up to 40 mg/ml which is well above the concentration to be expected in blood serum.

Figure 1:
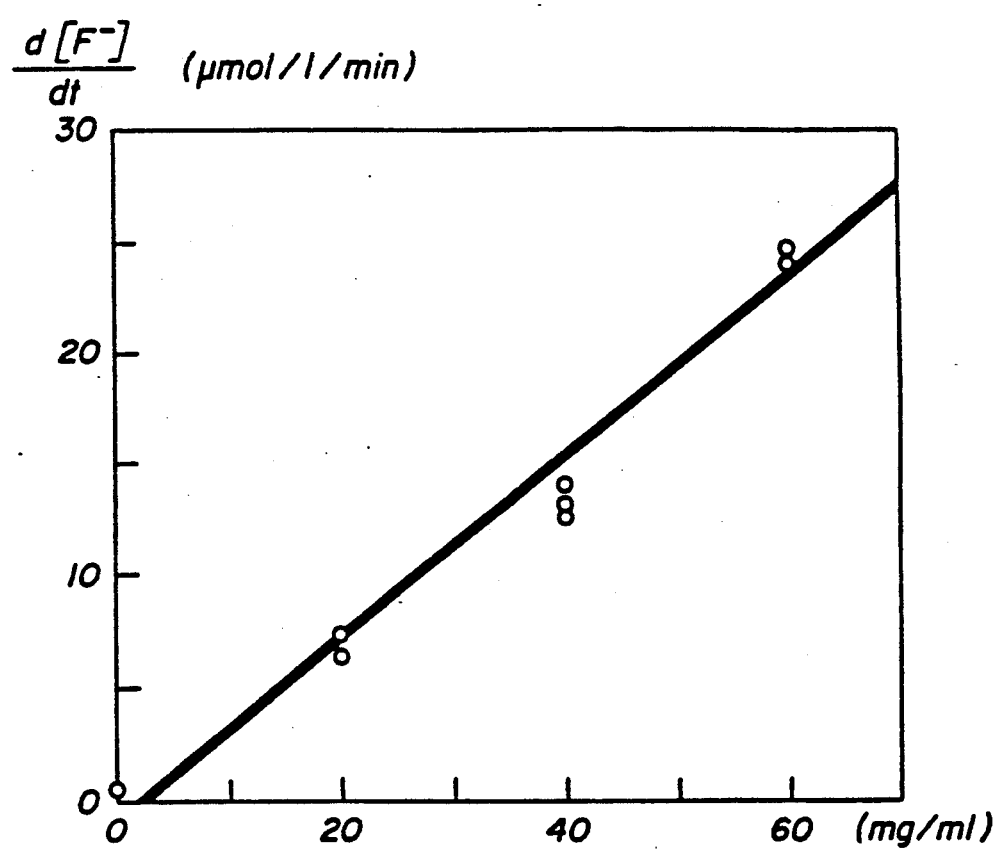
FIG. 1 is a calibration graph showing the variation of the rate of F$^-$ production as a function of the albumin concentration at pH 7.6 in phosphate buffer.

Unknown samples of blood serum were determined for albumin using the above procedure and checking against the curve of FIG. 1. Excellent correlation of the results and that from prior art methods was experienced.

EXAMPLE 2

Figure 2:
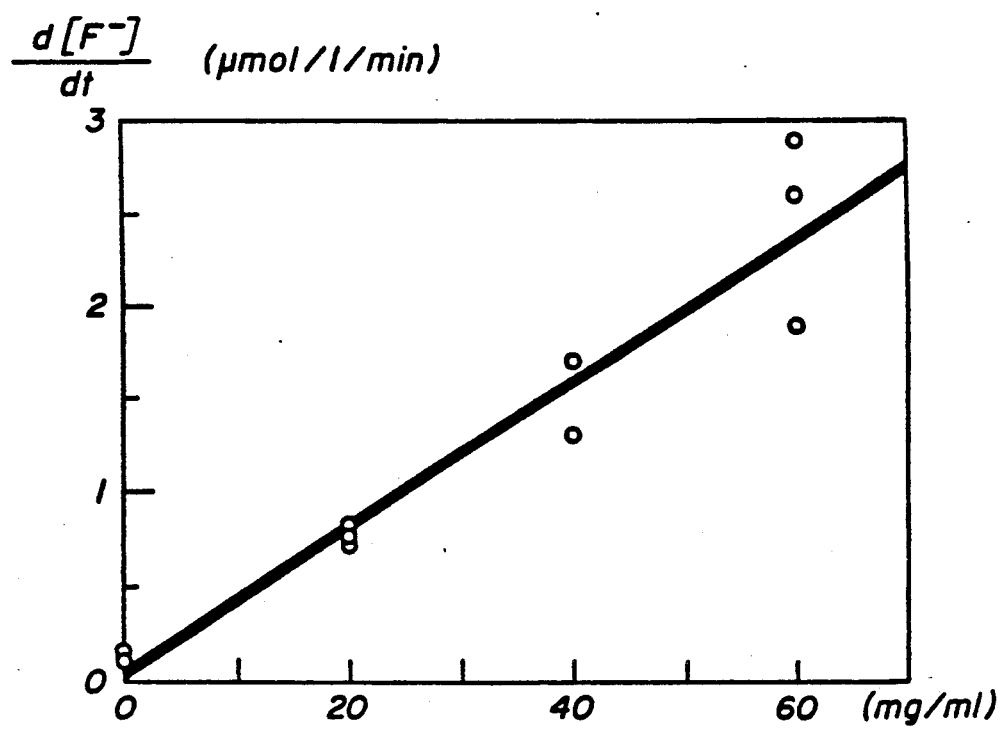
FIG. 2 is similar to FIG. 1 but for measurements run at pH 5.8.

The experiments reported in Example 1 were repeated but operating in phosphate buffer at pH 5.8. The pH of the serum remains the same as in Example 1. The results, as plotted in the graph of FIG. 2, are essentially similar to that of FIG. 1 but the rates are slower. The technique run at pH 5.8 is equally suitable for the determination of unknown but with lower sensitivity. The presence of globulin and other blood proteins, free aminoacids and urea did not interfere.

In addition to DNFB, other reagents of comparable propertie with regard to fluorine release are also usable e.g. dansyl fluoride of formula

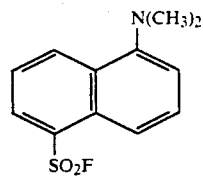

The following compounds are also possible: 2,4,6-trihalogeno-s-triazines of formulae

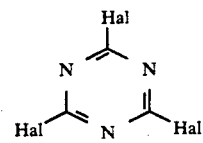

in which Hal represents fluorine chlorine or bromine and derivatives thereof in which one or two halogens are replaced by organic substituents.

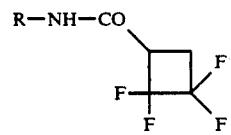

in which R is an organic group are derivatives of 2,2,3,3,-tetrafluorocyclobutane-1-carboxamide.

We claim:

1. A method for the quantitative determination of serum albumin in biological fluids even in the presence of globulins, comprising a first step of reacting a sample of serum with an excess of a halogeno-aromatic reagent in which at least one halogen atom is displaceable by the protein and the reaction leads to the formation of a protein/reagent complex; a second step of measuring the rate of halide ion liberation by an ion selective electrode; and a third step of computing the measured rate data with other similar data from the same reaction performed with calibrating amounts of albumin, such computation providing results on said determination.

2. The method of claim 1, in which the reagent is dinitro fluorobenzene (DNFB) or dansyl fluoride.

3. The method of claim 1, in which halide is fluoride which is measured with an F$^-$ selective electrode.

4. The method of claim 3, in which the buffer contains inorganic compounds and the pH is 5.8-7.6.

5. The method of claim 4 wherein the inorganic compounds are phosphates.

6. The method of claim 3, in which the reaction medium is buffered at pH 5.5-7.8.

7. The method of claim 6, in which the reagent is dissolved in an organic solvent and an aliquot of this solution is emulsified with said buffer.

8. The method of claim 6, in which the reagent is distributed homogeneously on a piece of porous material and thereafter, this porous material is contacted with the sample within the buffer.

9. A method for the quantitative determination of serum albumin in biological fluids even in the presence of globulins, comprising a first step of reacting a sample of serum with an excess of a halogeno-aromatic reagent selected from the group consisting of dinitro fluorobenzene (DNFB) or dansyl fluoride in which at least one fluorine atom is displaceable by the protein and the reaction leads to the formation of a protein/reagent complex; a second step of measuring the rate of fluoride ion liberation; and a third step of computing the measured rate data with other similar data from the same reaction performed with calibrating amounts of albumin, such computation providing results on said determination.

10. The method of claim 9, in which the fluoride is measured by an $F^-$ selective electrode.

11. The method of claim 10, in which the buffer contains inorganic compounds and the pH is 5.8–7.6.

12. The method of claim 11 wherein the inorganic compounds are phosphates.

13. The method of claim 10, in which the reaction medium is buffered at pH 5.5–7.8.

14. The method of claim 13, in which the reagent is dissolved in an organic solvent and an aliquot of this solution is emulsified with said buffer.

15. The method of claim 13, in which the reagent is distributed homogeneously on a piece of porous material and thereafter, this porous material is contacted with the sample within the buffer.

* * * * *